(12) United States Patent
Pelly

(10) Patent No.: US 7,906,082 B2
(45) Date of Patent: Mar. 15, 2011

(54) METHOD AND APPARATUS FOR REFINING BIODIESEL

(76) Inventor: Michael F. Pelly, Olympia, WA (US)

( * ) Notice: Subject to any disclaimer, the term of this patent is extended or adjusted under 35 U.S.C. 154(b) by 180 days.

(21) Appl. No.: 12/409,250

(22) Filed: Mar. 23, 2009

(65) Prior Publication Data

US 2010/0015020 A1     Jan. 21, 2010

Related U.S. Application Data

(63) Continuation of application No. 10/547,574, filed as application No. PCT/US2004/008294 on Mar. 17, 2004, now Pat. No. 7,507,846.

(60) Provisional application No. 60/456,097, filed on Mar. 20, 2003.

(51) Int. Cl.
*B01J 8/00* (2006.01)
*B01J 19/00* (2006.01)
*C07C 67/08* (2006.01)
*C07C 51/43* (2006.01)

(52) U.S. Cl. ......... 422/234; 422/224; 422/187; 554/170; 554/174; 560/98

(58) Field of Classification Search .................. 422/234, 422/224, 187; 554/170, 174; 560/98
See application file for complete search history.

(56) References Cited

U.S. PATENT DOCUMENTS

| | | | |
|---|---|---|---|
| 3,474,131 | A | 10/1969 | Schmerling |
| 3,927,982 | A | 12/1975 | Chapman |
| 5,399,731 | A | 3/1995 | Wimmer |
| 5,424,467 | A | 6/1995 | Bam |

(Continued)

FOREIGN PATENT DOCUMENTS

WO    WO 2004/085579    10/2004

OTHER PUBLICATIONS

U.S. Appl. No. 60/456,097, filed Mar. 20, 2003, Pelly.

(Continued)

*Primary Examiner* — Walter D Griffin
*Assistant Examiner* — Lessanework Seifu
(74) *Attorney, Agent, or Firm* — Barry L. Davison; Davis Wright Tremaine LLP

(57) ABSTRACT

Method and apparatus for producing biodiesel fuel, i.e., alkyl ester, from vegetable and/or animal oil. A transesterification catalyst is prepared in a base catalyst tank by spraying alkyl alcohol under pressure through jets at metal hydroxide pellets until the pellets have fully reacted with the alcohol. The oil is heated and transesterified in the presence of alkyl alcohol and the transesterification catalyst in a closed, recirculating transesterification flow system under slight cavitation to yield product alkyl ester and product glycerol. Cavitation is achieved by permitting air to enter the transesterification flow system through an adjustable air inlet valve. When permitted to stand, product alkyl ester forms an upper layer that is decanted and subjected to purification steps, to remove particulates and alkyl alcohol from the product alkyl ester, and a lower layer of product glycerol is drained away. Purification of the product alkyl ester preferably includes subjecting the product alkyl ester to an overhead water mist in a wash tank with simultaneous infusion of a stream of air bubbles. Alcohol vapor is reclaimed as liquid alcohol within an alcohol condenser and stored for reuse. If the oil contains free fatty acids, prior to transesterification, the oil is heated and the free fatty acids are esterified in the presence of an esterification catalyst and alkyl alcohol. For safety, baffles and explosion damper/flame arrestors are provided in locations where flammable vapors pose a risk.

27 Claims, 11 Drawing Sheets

U.S. PATENT DOCUMENTS

| | | |
|---|---|---|
| 5,468,887 A | 11/1995 | Gupta |
| 5,514,820 A | 5/1996 | Assmann |
| 5,972,057 A | 10/1999 | Hayafuji |
| 6,015,440 A | 1/2000 | Noureddini |
| 6,127,560 A | 10/2000 | Stidham |
| 6,262,285 B1 | 7/2001 | McDonald |
| 6,440,057 B1 | 8/2002 | Ergun |
| 7,507,846 B2 | 3/2009 | Pelly |

OTHER PUBLICATIONS

Knothe et al., "Biodiesel: The Use of Vegetable Oils and Their Derivatives as Alternative Diesel Fuels," Chapter 10 in *Fuels and Chemicals from Biomass*, 1997, American Chemical Society, Washington, D.C., pp. 172-207.

Konen et al., "Esterification of Unsaturated Fatty Acids," Journal of the American Oil Chemists' Society, 1945, pp. 57-60, vol. 22.

METHOD AND APPARATUS FOR REFINING BIODIESEL

CROSS REFERENCE TO RELATED APPLICATIONS

This application is a continuation of U.S. patent application Ser. No. 10/547,574 filed Aug. 31, 2005 (now patent 7,507,846 issued Mar. 24, 2009), which is a U.S. nationalization of PCT/US2004/008294 filed Mar. 17, 2004 (WO 2004/085579 published Oct. 7, 2004), which claims priority to 60/456,097 filed Mar. 20, 2003, all incorporated by reference herein.

STATEMENT REGARDING FEDERALLY APPROVED RESEARCH OR DEVELOPMENT

None.

BACKGROUND OF THE INVENTION

1. Field of the Invention

This invention relates generally to a method of producing biodiesel fuel oil, i.e., alkyl esters of triglycerides, from virgin or waste plant and/or animal oils. The invention also relates to an apparatus for producing biodiesel fuel oil from plant and/or animal oils employed for carrying out the production method.

2. Background Art

Diesel fuel derived from petroleum comprises hydrocarbon chains of 11 to 13 carbons. New vegetable oil, such as soybean, canola, corn, rapeseed, and cottonseed oil, has chains of about 18 carbons in the form of fatty acid triglycerides, usually in groups of three joined by a glycerol bridge. To burn in an engine, the carbon chains need to be broken down to be similar in length to fossil fuel diesel. This has been accomplished by transesterifying the fatty acid triglycerides in the presence of a catalyst and alkyl alcohol to yield alkyl ester and glycerol:

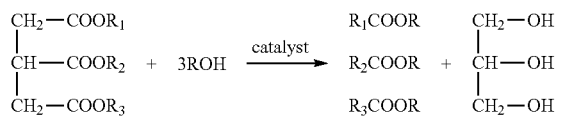

Product alkyl ester is separated from the product glycerol, washed and filtered. If vegetable and/or animal oil was used for cooking, it typically also contains free fatty acids and water; in that case, prior to the transesterification reaction, the water is removed and the oil is subjected to esterification in the presence of an esterification catalyst and alkyl alcohol to esterify the free fatty acids. The triglyceride/alkyl ester mixture is then subjected to transesterification. Thereafter, the product alkyl ester is separated from the product glycerol and purified by washing and filtering.

Prior to the present invention, in processes for manufacturing fatty acid esters useful as engine fuel by transesterification of oil or grease of vegetable or animal origin in the presence of a catalyst, it was known to create a methanol/catalyst feed solution for adding with agitation to the triglycerides, and to warm the triglycerides in preparation for the transesterification reaction. U.S. Pat. No. 6,262,285 B1 to McDonald; U.S. Pat. No. 5,972,057 to Hayafuji et al. It was also known to use as a transesterification catalyst an alkali catalyst, such as sodium hydroxide or sodium methoxide, U.S. Pat. No. 5,399,731 to Wimmer, and to strain the triglycerides prior to sending the triglycerides to a reaction vessel for transesterification; U.S. Pat. No. 5,972,057 to Hayafujji et al. It was further known that the product alkyl esters, being less dense, would, if left to stand, come to overlie the product glycerol, such that the product alkyl ester could be decanted or drawn off from the top of the reaction vessel, and the glycerol could be drained from the bottom of the reaction vessel; U.S. Pat. No. 6,262,285 B1 to McDonald and U.S. Pat. No. 5,399,731 to Wimmer. It was further understood that methanol and methoxide vapor could be recovered from the reaction vessel by condensing it and then reusing it in the transesterification reaction; U.S. Pat. No. 6,262,285 B1 to McDonald; U.S. Pat. No. 5,468,997 to Gupta; U.S. Pat. No. 5,424,467 to Bam et al. Stidham et al. in U.S. Pat. No. 6,127,560, Hayafuji in U.S. Pat. No. 5,972,057 and Wimmer in U.S. Pat. No. 5,399,731 disclosed processes to wash impurities such as soap particles from the product alkyl ester. It was also known to use a heat exchanger to add heat to the transesterification reaction; U.S. Pat. No. 6,015,440 to Noureddini.

One distinctive feature of the present invention is its rapidity of transesterification, which is achieved, in part, by continuously recirculating the reaction mixture, comprised of triglycerides, alkyl alcohol and transesterification catalyst, from a reaction vessel, through external recirculation means that includes a low pressure main pump and back into the reaction vessel, while at the same time agitating the reaction mixture within the external circulation means with a stream of air bubbles produced by cavitation. Ergün et al, U.S. Pat. No. 6,440,057 B1, has disclosed a method and apparatus for producing fatty acid methyl ester from a mixture of vegetable and/or animal fatty acids with an alkaline solution dissolved in alcohol, wherein border surfaces of the mixture are enlarged by dynamic turbulence in a reaction section and the transesterification is performed under pressure. Although Ergün et al. suggest cavitation emulsification as one means to achieve dynamic turbulence in the mixture, their cavitation is performed without continuous recirculation of the mixture and does not introduce a stream of air bubbles into the reaction mixture. Instead, Ergün et al. introduce cavitation within a continuous, one-way flow system, wherein the mixture flows under applied pressure through a pipe packed with loose balls and the like or through a coiled pipe dynamic emulsifier. To force the mixture through a pipe packed with loose balls or through the tortuous path presented by a coiled pipe requires a relatively high applied pressure. Thus, an advantage of the present invention, which applies relatively low pressure to the mixture, when compared to that of Ergün et al., is that the quantity of mixture subjected to transesterification can be scaled up several fold without the necessity of increasing the size of the main pump as would be required if a high applied pressure were required. Operator safety is also of primary concern. The chemicals used in esterification of free fatty acids and transesterification of triglycerides are hazardous; accordingly, use of a low pressure main pump in the present invention reduces the risk of bodily harm to an operator who happens to be in the vicinity of a leak in the apparatus during esterification and/or transesterification reactions. Operator safety is further enhanced by retaining the mixture during the transesterification reaction within a closed transesterification flow system, and by venting hazardous fumes through a vent pipe in an upper portion of the reaction vessel. A flame arrestor is also provided to decrease the risk of fire or explosion. Such safety features appear to be made available for the first time with the present invention.

SUMMARY OF THE INVENTION

Accordingly, it is an object of the invention to provide a method and apparatus for converting triglycerides present in vegetable and/or animal oil, consisting essentially of triglycerides, by transesterification into allyl ester suitable for use as diesel fuel.

In the case of vegetable and/or animal oil that, in addition to triglycerides, also contains water and free fatty acids, it is a further object of the invention to provide a method and apparatus for removing the water and converting said free fatty acids to product alkyl ester by esterification of the free fatty acids, and thereafter subjecting the oil/alkyl ester mixture to transesterification to convert the triglycerides to alkyl ester suitable for use as diesel fuel.

A further object of the invention, is to provide a method and apparatus that enhances operator safety by containing within a closed flow system, and by venting to the atmosphere, noxious fumes that arise during esterification of free fatty acids and during transesterification of triglycerides.

A still further object is to provide such a method and apparatus wherein rapid transesterification of triglycerides to product alkyl ester is achieved, in part, by continuously recirculating a reaction mixture comprised of oil, a transesterification catalyst, and alkyl alcohol, from a reaction vessel, through a convoluted, external recirculation means that includes a low pressure main pump and back into the reaction vessel, while at the same time agitating the reaction mixture within the external circulation means with a stream of air bubbles produced by cavitation valve means.

Another object of the invention is to create at the location where transesterification of triglycerides is to be carried out, an effective transesterification catalyst by combining and mixing with swirling in a conical-bottomed base catalyst tank metal hydroxide pellets with alkyl alcohol, the alcohol being directed under pressure through jets angled tangentially and downwardly toward the pellets in the conical bottom, said alkyl alcohol being methanol or ethanol and said pellets being sodium hydroxide or potassium hydroxide, whereby sodium methoxide, potassium methoxide or potassium ethoxide is formed for use as a transesterification catalyst.

A further object of the invention is to provide an alcohol recovery system for recovering liquid alkyl alcohol for reuse in the invention by drawing under vacuum alcohol vapor through a condenser from the reaction vessel and from other parts of the invention. The vacuum is created either by a vacuum pump or by a main pump connected in series with cavitation valve means that communicates with the condenser and the main pump. The cavitation valve means includes a one-way check valve and an adjustable air valve that permits air to recirculate through the apparatus of the invention.

It is still a further object of the invention, to provide a flame arrestor to minimize the risk of fire or explosion during the refining of alkyl ester from vegetable and/or animal oil.

To accomplish the foregoing objects, according to this invention, a first, basic method and apparatus is provided to obtain alkyl ester suitable for use as a diesel fuel oil from vegetable and/or animal oil consisting essentially of triglycerides and containing little or no free fatty acids or water. The oil is preheated to between 27 and 100 degrees C. in a preheater vessel and pH is adjusted to 8.7 to 8.9. A closed, recirculating transesterification flow system is provided. The transesterification flow system includes a reaction vessel and a main pump external to the reaction vessel having an inlet port for receiving reaction mixture from the reaction vessel and an outlet port for pumping the reaction mixture back into the reaction vessel, whereby the reaction mixture is recirculated during the transesterification reaction. The transesterification flow system further includes cavitation valve means connected to the inlet port of the main pump. The cavitation valve means includes a one-way check valve and an adjustable air inlet valve connected in series with the inlet port of the main pump. In a version of the invention that does not include recovery of alcohol, atmospheric air enters the transesterification flow system through an adjustable air inlet valve. In a version of the invention that includes an alcohol recovery system, air is drawn under vacuum from the reaction vessel, through an alcohol condenser, an adjustable air inlet valve, a one way check valve, to the inlet port of the main pump and thence recirculated through the outlet port of the main pump back to the reaction vessel. Using the main pump this way can eliminate the need for a separate vacuum pump, if desired.

To start the transesterification reaction, the preheated, pH-adjusted oil is introduced into the transesterification flow system and combined with alkyl alcohol in stoichiometric excess in the presence of an effective transesterification catalyst thereby forming a mixture. The check valve and air inlet valve are opened sufficiently to permit a stream of air bubbles to enter into the system, which creates a slight cavitation throughout the flow system, thereby accelerating the transesterification reaction. The reaction is permitted to proceed until there is formed a reaction mixture comprised of product alkyl ester and product glycerol. Reaction mixture is preferably conducted to and from the reaction vessel by transparent hoses, which permits visual monitoring of the transesterification reaction: when the color of the mixture entering the reaction vessel is substantially the same as the color of the mixture exiting the reaction vessel, the reaction is complete. The reaction mixture is then permitted to separate into an upper phase of product alkyl ester overlying a lower phase of a mixture of particulates and product glycerol. The glycerol is drained away. The product alkyl ester is decanted and is filtered to remove particulates; the filtered alkyl ester constitutes an unwashed biodiesel fuel. If permitted to stand long enough, eventually any soap contaminants will settle to the bottom. Suitable alkyl alcohols for the transesterification reaction include methanol and ethanol. An effective transesterification catalyst is preferably chosen from sodium methoxide, potassium methoxide and potassium ethoxide. Such hazardous substances are advantageously and preferably formed at the site of the transesterification flow system immediately prior to commencing the transesterification reaction. Accordingly, a method and apparatus for forming an effective transesterification catalyst is provided. Metal hydroxide pellets chosen from sodium hydroxide and potassium hydroxide are combined in a base catalyst tank with sufficient alkyl alcohol to attain a stoichiometric ration of alkyl alcohol to oil. The combination is swirled to induce complete mixing and reaction of the metal hydroxide pellets with the alkyl alcohol to form a metal alkoxide catalyst—that is, sodium methoxide, potassium methoxide or potassium ethoxide. The base catalyst tank has a conical bottom. The alkyl alcohol is preferably introduced under pressure into the conical bottom through a plurality of spaced-apart jets angled tangentially and downward to induce swirling of the alkyl alcohol and pellets. To further enhance the mixing and reaction of the alkyl alcohol and the metal hydroxide pellets, the alkyl alcohol and alkoxide mixture in the base catalyst tank continuously exits through an exit port in the conical bottom, passes through an external alcohol/alkoxide circulation means, and reenters the tank through the jets. A pellet screen is provided to cover the exit port in the conical bottom to prevent the pellets from exiting the base catalyst tank before they are completely in solution with alcohol.

A second method and apparatus is also provided, substantially similar to the first, wherein after the transesterification reaction is completed, the reaction mixture is preferably conducted through a chiller to reduce the temperature of the reaction mixture and thence to a temporary holding tank to permit the reaction mixture to separate into an upper phase of product alkyl ester overlying a lower phase mixture of particulates and product glycerol. The advantage of the temporary holding tank is that several batches of reaction mixture can be accumulated prior to purifying the accumulated reaction mixture by washing, settling and filtering. The product alkyl ester is next drawn off from the temporary holding tank and washed by water mist in a wash tank while, simultaneously, air bubbles are introduced into the bottom of the wash tank to facilitate settling out of soaps and particulates. The wash tank is equipped with a floating pickup for drawing off the washed alkyl ester to a settling tank where the washed alkyl ester is permitted to separate into an upper phase of alkyl ester overlying a lower phase mixture of soaps and particulates. The floating pickup draws from just below the surface to avoid surface scum. The product alkyl ester is decanted from the settling tank and filtered to remove particulates.

To recover alkyl alcohol for reuse, an alcohol recovery system conducts alkyl alcohol vapor under vacuum from an upper portion of the temporary holding tank, an upper portion of the reaction vessel, and an upper portion of the methanol glycerol separation vessel to an alcohol condenser. Liquid alcohol recovered in the condenser flows through a drain trap air lock and thence to a reclaimed alcohol tank for storage and reuse. The vacuum for recovering alcohol is created by the main pump or, alternatively, by a vacuum pump that performs double duty by also providing the stream of air bubbles for the wash tank.

For obtaining alkyl ester from vegetable and/or oil that includes free fatty acids and water, there is optionally provided a closed, recirculating flow, esterification flow system that includes an esterification reaction vessel and an acid pump for receiving an esterification reaction mixture from a lower portion of said vessel and returning said mixture to an upper portion of said vessel. The oil is preheated to between 27 and 100 degrees C. The preheated oil is allowed to stand long enough for any water in the oil to separate into a lower layer. The water is drained and the preheated oil is chilled down to 27 degrees C., more or less. The chilled oil is combined and mixed with at least a stoichiometric amount of alkyl alcohol in the esterification flow system. An effective esterification catalyst is added to the esterification flow system to esterify the free fatty acids to obtain a mixture of product alkyl ester and unreacted triglycerides. The esterification reaction is permitted to proceed for at least 30 minutes at 32 to 38 degrees C. The recirculating flow is discontinued and glycerol is permitted to separate and form a lower layer below an upper layer of alkyl ester and unreacted triglycerides. The mixture of alkyl ester and unreacted triglycerides is then introduced into the transesterification flow system for processing as described above. Other objects, features and advantages of the invention will become apparent in the course of the following description with reference to the accompanying drawings.

Figure 9:
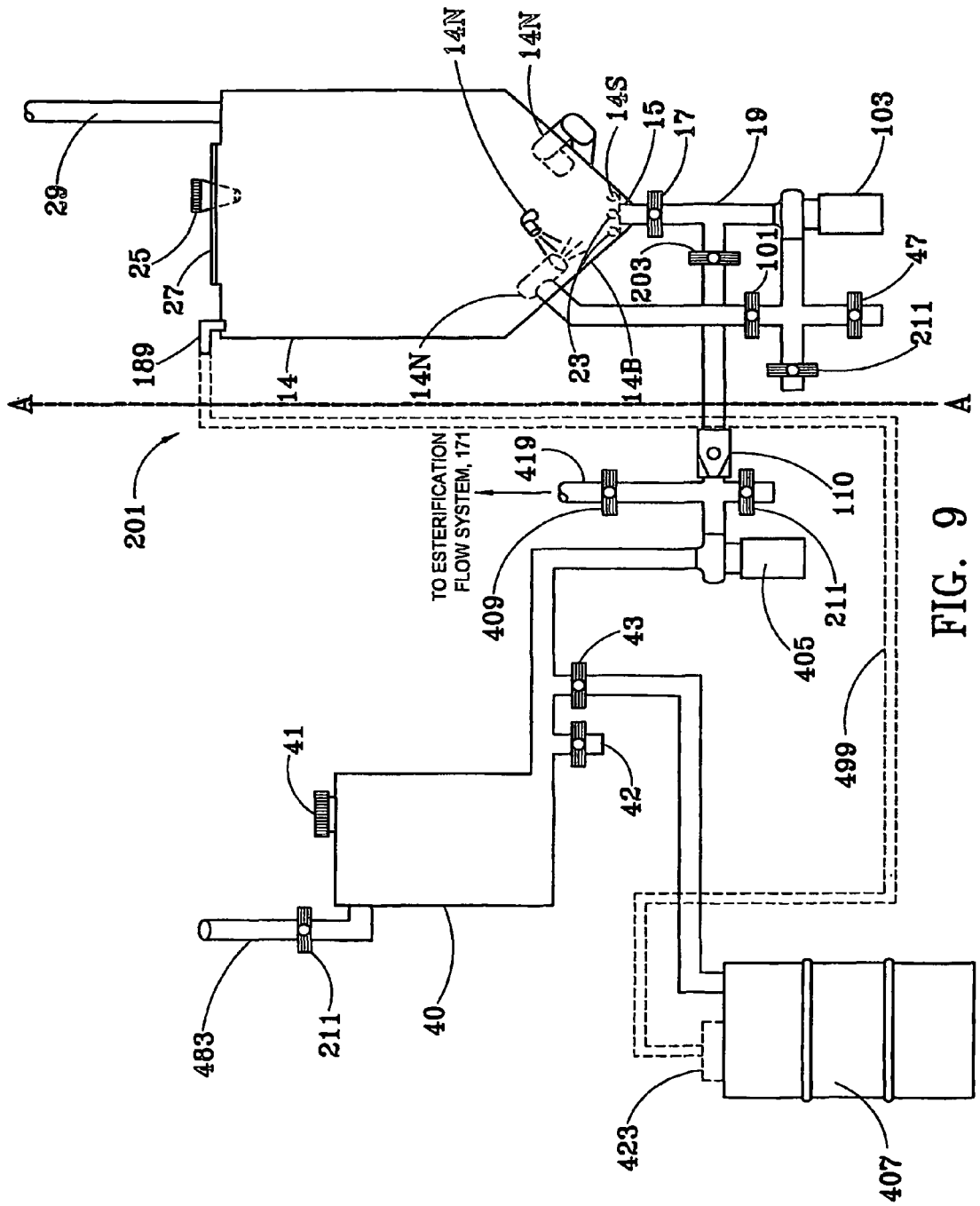
FIG. 9 is a schematic view of the alcohol delivery and catalyst mixing system.

Except where otherwise noted, similar elements are denoted by the same numeral throughout the several views; for instance, the numeral 211 generically refers to shut off valves. The apparatus of the invention illustrated to the right of the vertical line A-A in FIG. 9 is only a portion of the transesterification flow system—namely, the portion used in production of a metal alkoxide transesterification catalyst.

MODES FOR CARRYING OUT THE INVENTION

Figure 1:
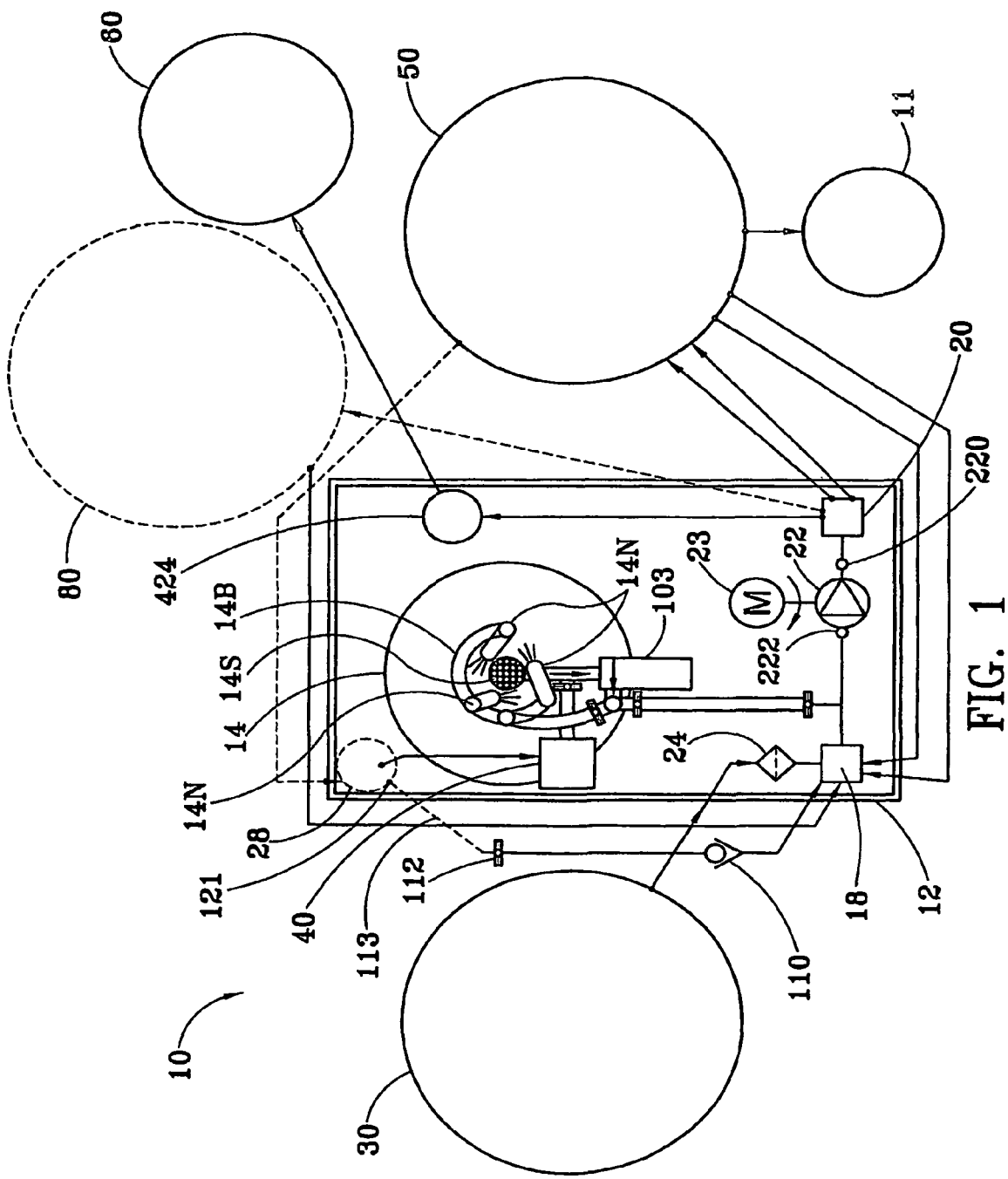
FIG. 1 is a schematic depiction in plan view of a first apparatus for converting into alkyl ester vegetable and/or animal oil, consisting essentially of triglycerides, to alkyl ester, and depicting optional additional apparatus in dashed outline.
Figure 10:
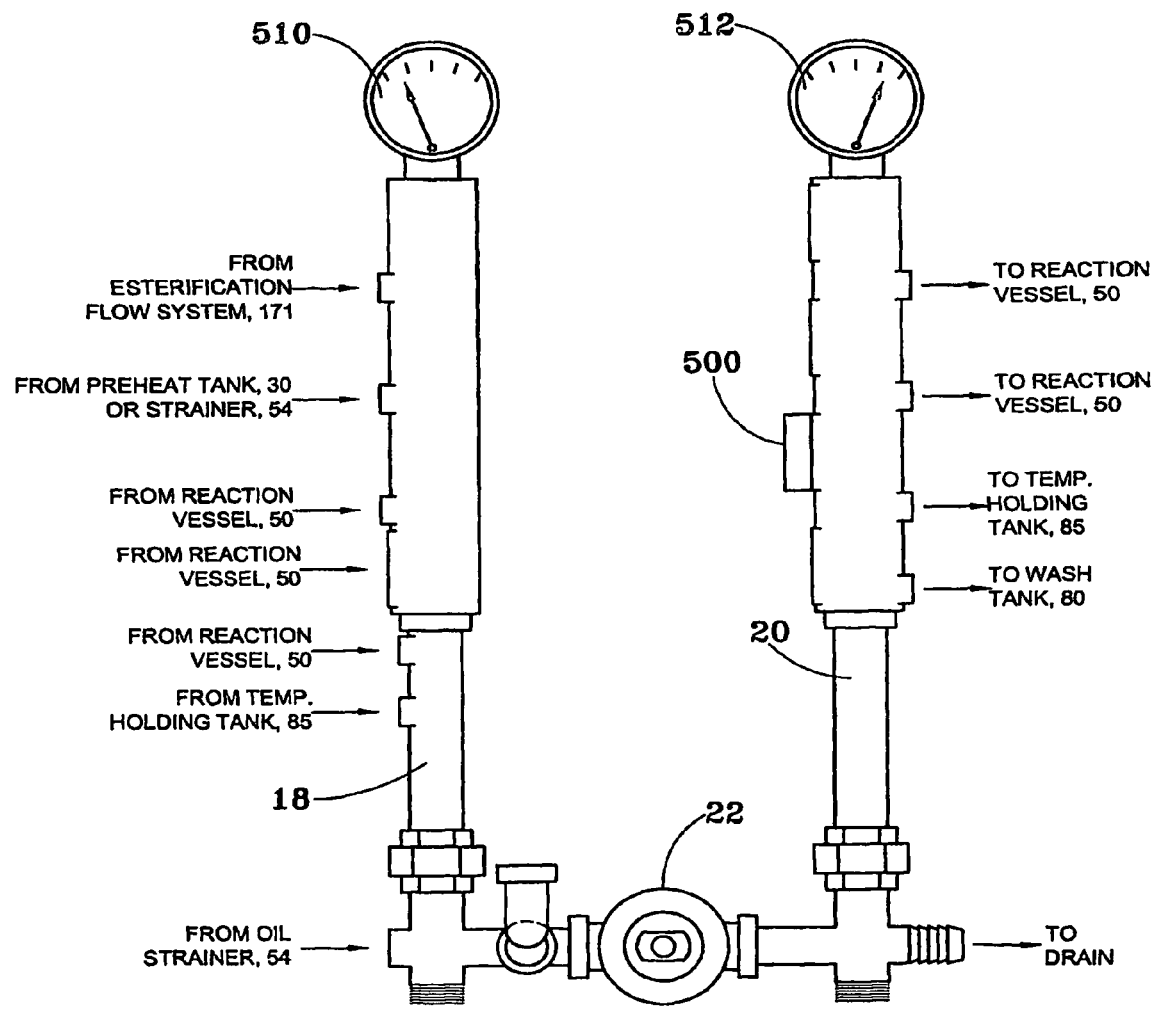
FIG. 10 is exemplary of the manifolds of the invention and depicts the main pump interposed between and connected to the first intake manifold and the first exhaust manifold.

Referring to FIG. 1, depicted in plan view is a first embodiment of the apparatus of the present invention intended for creating biodiesel fuel by transesterification of vegetable and/or animal oil consisting essentially of triglycerides, denoted generally by the numeral 10. Mounted to a processor pod 12 is a base catalyst tank 14 having a conical bottom 14B for combining and mixing metal hydroxide pellets with alkyl alcohol to form transesterification catalyst—either sodium methoxide, potassium methoxide or potassium ethoxide. The processor pod 12 also houses an alcohol reservoir 40, a first intake manifold 18, a first exhaust manifold 20, a main pump 22 in driven engagement with an electric motor 23, an oil input strainer 24, a filter 424 for removing particulates from product alkyl ester, and optionally an alcohol condenser 28, and a switch panel (not shown) for electrically activating the various electrical components and valves of the invention. If it is desired to automate the operation of the invention, the processor pod 12 can further house microprocessor means (not shown) that will activate and deactivate said various electrical components and valves of the invention at appropriate times and according to a programmed instruction set. As may be seen in FIG. 10, a vacuum gauge 510 is mounted to the first intake manifold 18 and a combination pressure and temperature gauge 512 is mounted to the first exhaust manifold 20. A pressure-sensing switch 500 is also mounted to the first exhaust manifold 20 to shut off power to the main pump 22 when there is no flow through said manifold 20. Adjacent the processor pod 12 is an oil preheater and dewatering tank 30 for storing, dewatering, and heating vegetable and/or animal oil preparatory to refining it into biodiesel fuel. Also exterior to the processor pod 12 are a transesterification reaction vessel 50, a day tank 60 for receiving and storing product alkyl ester, and a glycerol storage tank 11. Although not required for operation of the invention, additional components may optionally be incorporated into the invention for enhanced efficiency of operation and to obtain a higher quality of product alkyl ester, as depicted in dashed outline in FIG.

1—namely, an alcohol condenser 28 that is part of an alcohol recovery system 61 and a wash tank 80 for purifying product alkyl ester.

Figure 3:
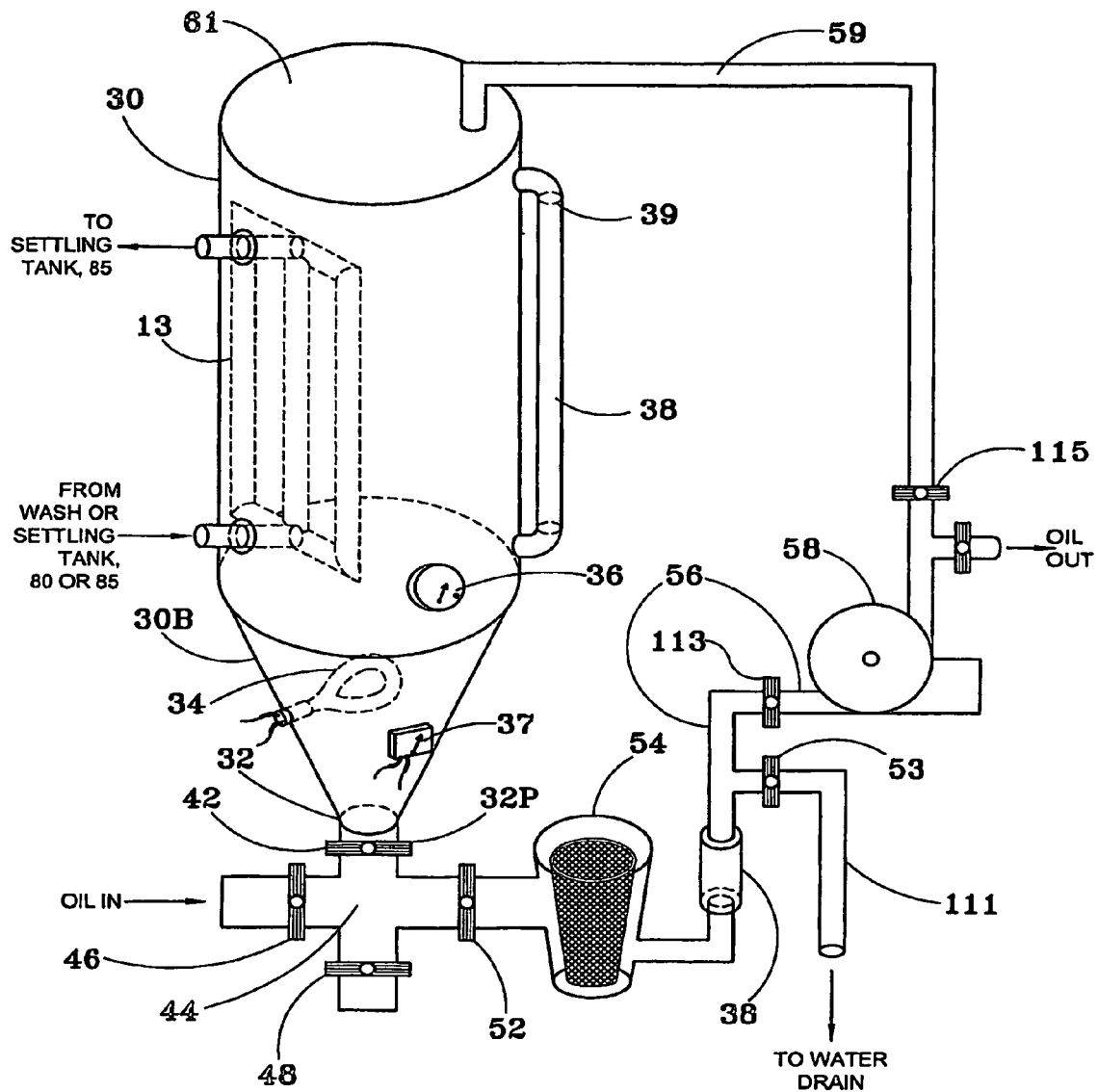
FIG. 3 is a schematic, elevational view of an oil pre-heater and de-watering vessel and associated oil recirculation system.

The preheater and dewatering tank 30 is depicted in schematic, elevational view in FIG. 3, and comprises a closed, substantially cylindrical tank with a conical bottom 30B that terminates in an outlet port 32. Inserted into the interior of the conical bottom 30B is an electric resistance heater 34 for heating oil within the tank to between 27 and 100 degrees C. A temperature gauge 36 is mounted on the exterior of the tank 30 for monitoring the temperature of the oil inside said tank. An electric thermostat 37 is also mounted on the exterior of the tank 30 for adjusting the temperature of the oil inside the tank 30 by controlling the amount of electric power delivered to the electric resistance heater 34. Alternatively, the oil can be heated by other means, such as by a propane burner or boiler. A transparent site tube 38 is mounted vertically to an exterior wall of the tank 30. The site tube 38 has upper and lower ends that intrude into the interior of the tank 30, which allows an operator to monitor the oil level 39 in the interior of the tank 30. A lower outlet port 32P at the bottom 32 is joined to a four-way union 44 through a shut-off valve 42. Three additional shut-off valves 46, 48, 52 are attached to the remaining outlets of the union 44. When valves 42 and 52 are open, oil flows from the tank 30 through a strainer 54 and through piping 56 to an oil pump 58 and thence through a refill pipe 59 for reentry to the tank 30 through the tank ceiling 61. This arrangement permits continuous circulation of the oil into and out of the tank 30 to promote uniform heating of the oil preparatory to transesterification. Optionally, there may be disposed within the interior of the tank 30 a heat exchanger 13, which, during the preheat stage of a current batch of oil, is bathed in heated oil and transmits heat to product alkyl ester circulated through the heat exchanger 13 that was produced by transesterification of a prior batch of oil. Heating the alkyl ester promotes its purification in the washing and settling phases of refinement. The heater 34 is turned off, and the oil is permitted to stand 10 to 30 minutes. Any water that may have been in the oil collects in the conical bottom 30B. Valve 42, valve 52 and valve 53 are opened to permit water to pass through the site tube 38 and out drain tube 111 until oil is sighted flowing through the site tube 38. Valve 53 is then closed. Valve 113 and valve 115 are opened to permit pump 58 to recirculate heated oil through the tank 61 to remix the oil. An oil sample is obtained from the drain tube 111 by temporarily opening the valve 53 and the pH of the oil is measured. The quantity of metal hydroxide to be added to the oil is determined as a function of the pH of the oil. The more acidic the oil, the more metal hydroxide is necessary to achieve the desired pH range of 8.7 to 8.9 during the transesterification reaction. For example, fresh canola oil requires about 3.5 g. sodium hydroxide or 4.9 g. potassium hydroxide to achieve the desired pH range. The required quantity of metal hydroxide is then introduced into the base catalyst tank 14 for the intended number of liters of oil that are to be transesterified in a single batch.

As shown in FIGS. 1 and 9, the base catalyst tank 14 has a plurality of nozzles 14N directed tangentially and downwardly towards the conical bottom 14B. The conical bottom 14B terminates in an outlet port 15 that communicates through shutoff valve 17 with a three-way tee 19. A horizontal screen 14S overlies the outlet port 15 and supports metal hydroxide pellets 23 that are introduced into the tank 14 through a lidded funnel 25 opening in the top of the tank 14. A vertical vent tube 29 extends upwards through the top of the tank 14 to permit escape of noxious vapors from the tank 14 to the atmosphere. The alcohol can be pumped directly via pipe 499 into the base catalyst tank 14 through an inlet port 189 by a pump 423 mounted to the top of the methanol storage drum 407, as shown in FIG. 9. Alternatively, alkyl alcohol is added to an alcohol primer tank 40 through primer cap 41 or through inlet pipe by opening valve 43, with the primer tank drain valve 42 shut. The alcohol primer tank 40 can be drained through the tank drain valve 42. With the pump 405 activated, valves 17 and 47 closed and valves 203 and 101 open, the mixer pump 103 accepts alcohol from pump 405; pump 405 is activated and pumps alcohol under pressure past a check valve 110 through nozzles 14N into the tank 14 until a desired alcohol level is achieved therein, at which point the valve 203 is closed and valve 17 is opened. Then, the mixer pump 103 recirculates alcohol under pressure through the base catalyst tank 14. Thus, regardless of how alcohol is introduced into the tank 14, the mixer pump 103, when activated, causes the alcohol to be sprayed through the nozzles 14N onto the metal hydroxide pellets 23 and to be recirculated into, through, and out of the tank 14. As the pellets react with the alcohol to form alkoxide, the mixture of alkoxide and alcohol drains through the screen 14S and is recirculated from the mixer pump 103 back through the base catalyst tank 14; unreacted pellets 23 meanwhile are retained by the screen 14S until fully reacted. Once the pellets are fully reacted with the alkyl alcohol, the product alkoxide is ready for catalytic use in the transesterification system.

A closed, recirculating transesterification system 201 is provided that includes a reaction vessel 50, a first intake manifold 18, a first exhaust manifold 20, and a main pump 22 disposed between said intake and exhaust manifolds. As may best be seen in FIG. 4, the reaction vessel 50 has an inlet port 52 and an inlet tube 52T attached thereto in an upper portion and two outlet ports 254, 256 in a lower portion above a conical bottom 50B. The upper outlet port 256 is disposed to permit removal of the liquid contents of the vessel above the conical bottom 50B through piping (not shown) to return said liquid contents to the inlet port 22*i* of the main pump 22 through first intake manifold 18. A draw tube 54T communicates with lower inlet port 254 and extends down into the conical bottom 50B, whereby the liquid contents of the conical bottom can be withdrawn and through piping (not shown) returned to the inlet port 22*i* of the main pump 22 through first intake manifold 18. Use of the draw tube 54T in this way helps keep the glycerol warm and circulating, and thereby lessens the chance that the glycerol will gel. A transparent site tube 38 is mounted vertically to an exterior wall of the reaction vessel 50. The site tube 38 has upper and lower ends that intrude into the interior of the tank 50, which allows an operator to monitor the transesterification reaction. When the color of the oil entering the reaction vessel 50 equals the color of the oil leaving it, the transesterification reaction is considered complete. When animal and/or vegetable oil consisting essentially of triglycerides is to be esterified, the heated oil is to be transesterified, the oil is permitted to enter the first intake manifold 18 and thence to be drawn by action of the main pump together with transesterification catalyst through the main pump, out the first exhaust manifold 20 back into an upper portion of the reaction vessel through inlet tube 50T. The transesterification system thereby accomplishes a closed, continuous circulation of the reaction mixture for thorough mixing of the oil with catalyst and to aid transesterification of the oil. Optionally, the reaction vessel 50 can include an electric resistance heater 155 to heat and maintain the temperature of the reaction mixture.

To further aid the transesterification reaction, cavitation means is also included in the closed, transesterification flow system 201. Said means includes a check valve 110 and an air inlet valve 112, as shown in FIG. 1. If the apparatus does not include an alcohol recovery system, the air inlet valve 112 and the check valve are simply connected in series to the inlet side of the first intake manifold 18 and the air inlet valve 112 is partially opened during the transesterification reaction just enough to permit a stream of air bubbles to enter from the atmosphere into the transesterification flow system 201 and for a slight cavitation to occur. It is found that slight cavitation significantly speeds the transesterification reaction within a closed, recirculating transesterification system. Alternatively, if an alcohol recovery system 161 is included, as shown by the dashed line 113, the one way check valve 110 and the air inlet valve 112 are connected in series with an outlet port 121 of an alcohol condenser 28 such that a stream of air bubbles is introduced into the transesterification flow system 201 utilizing air drawn from the condenser 28 and, ultimately, from the reaction vessel 50 to maintain a closed flow system (aided by a drain trap air lock 482 discussed below). Air may be drawn from the condenser 28 by a separate vacuum pump 175, but, in practice, it is found that the main pump 22 adequately creates a vacuum for this purpose during the transesterification reaction. Following transesterification, the product alkyl ester is permitted to separate out from the glycerol and particulates. The glycerol is drained and the product alkyl ester is filtered to remove particulates and stored in a day tank 60.

Figure 5:
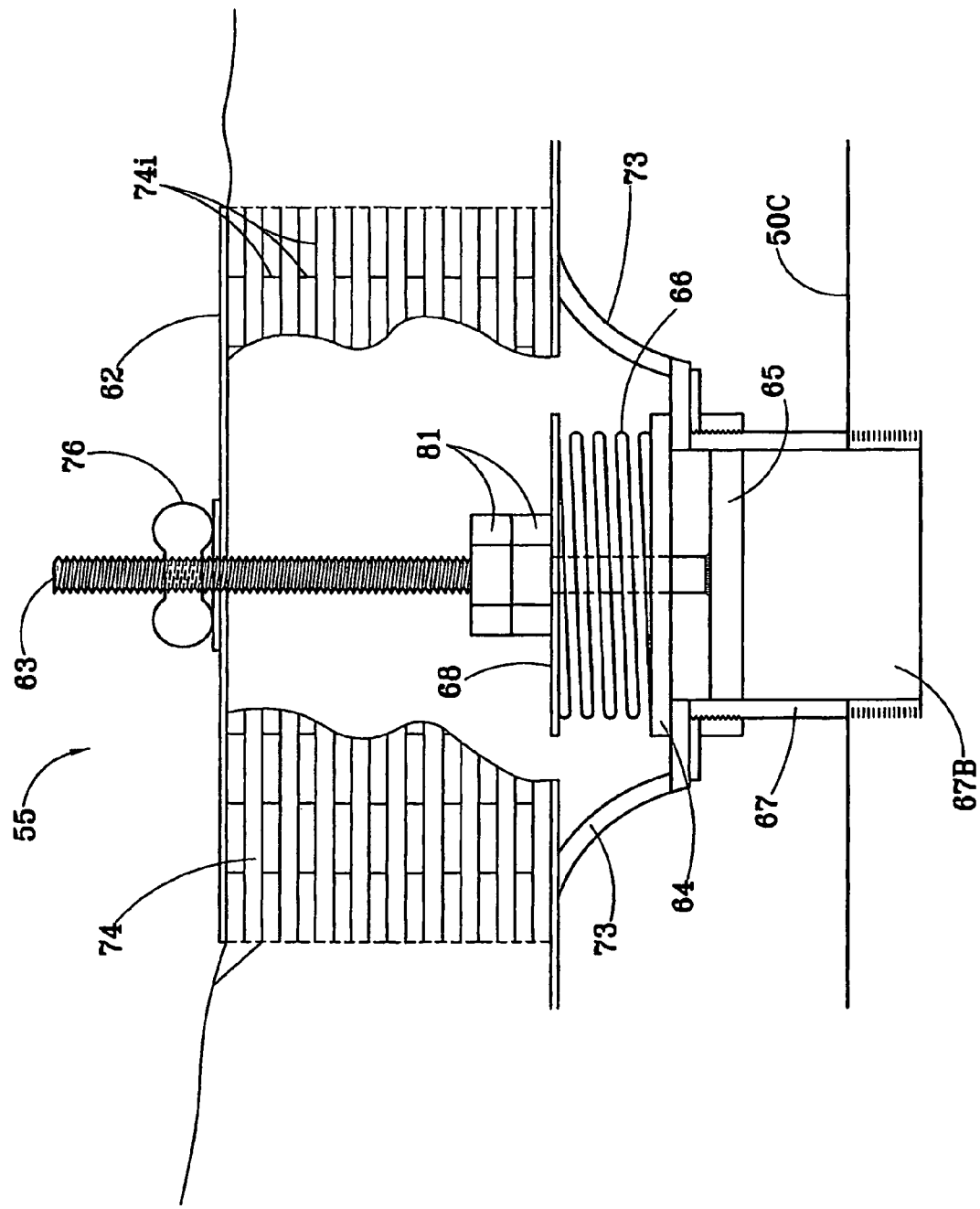
FIG. 5 is an enlarged, cut away view of an explosion dampener and flame arrester.
Figure 6:
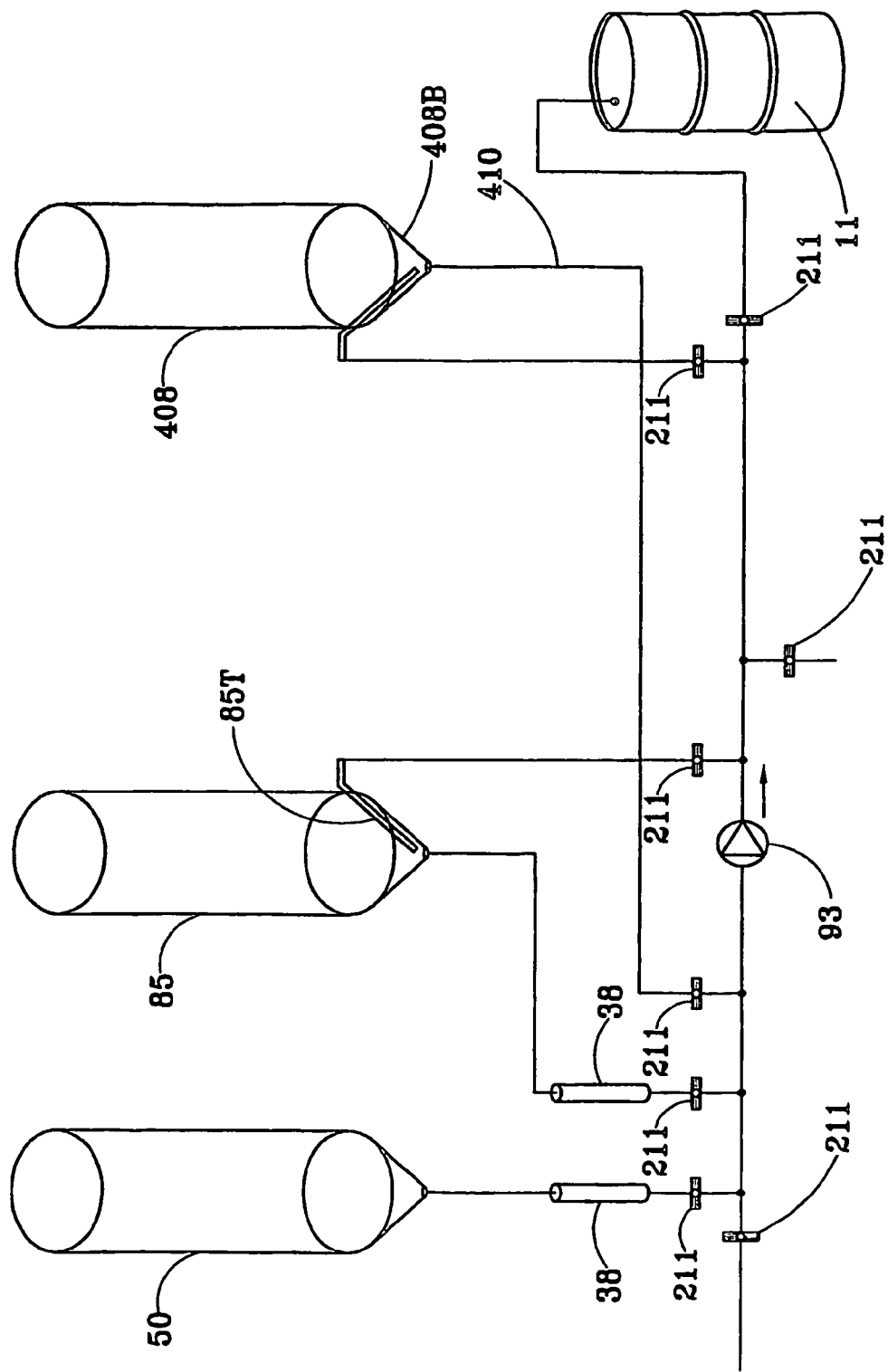
FIG. 6 is a schematic view of the glycerol handling system.

Although the foregoing description of the invention will produce alkyl ester suitable for use as biodiesel fuel, the quality of the biodiesel, the efficiency of the refining process, and the safety of the process can be improved by additional components and systems incorporated into the invention. To improve safety, the reaction vessel 50 preferably further includes an explosion damper and flame arrester 55 attached to the cover 50C of the vessel. As may be seen in FIG. 5, the explosion damper and flame arrester 55 is received in a threaded opening in the cover 50C and includes a top plate 62 having an aperture through which is inserted a vertical shaft 63. Below, and coaxially-aligned with the shaft 63, is a cylinder 67 open at a bottom end 67B but normally closed at a top end by a spring-loaded flapper 64 having an aperture through which is inserted a lower end of said shaft 63. The lower end of shaft 63 is joined to a horizontal support bar 65 attached to and extending across the interior of the cylinder 67. The bar 65 is sufficiently narrow that it does not occlude the interior space of the cylinder 67. An opposite, upper portion of the shaft 63 is threaded and extends above the top plate 62. A helical coil spring 66 is also coaxially-aligned with the shaft 63 and is maintained in compression against the flapper 64 by a washer 68 held in place by a pair of adjusting nuts 81 threaded onto the upper, threaded portion of shaft 63. The cylinder 67 is joined to the top plate 62 by a ring base 73 that simultaneously supports a horizontal, parallel stack of flat, metal strips 74 disposed between the ring base 73 and the top plate 62. A wing nut 76 threaded onto an upper end of the shaft 63 holds the shaft 63 firmly in position. In the event of an explosion within the reaction vessel 50, expanding, burning gases force the flapper 64 upward against the urging of the spring 66, thereby permitting the release of the burning gases into the interstices 74i between the metal plates 74, which suppresses the explosion and any accompanying flames. When the explosion subsides, the spring 66 lowers such that the reaction vessel 50 is once again closed. An explosion damper and flame arrester of the kind herein described is available from Hoerbiger Service, Inc., of Pampano Beach, Fla., as model number 98EV or model number 122EV.

A purer biodiesel can be obtained if the reaction mixture in the transesterification flow system 201 is made to pass through additional processing stages prior to filtering out precipitates. Referring to FIGS. 2 and 6-8, the reaction mixture is first conducted to a temporary holding tank 85 where the reaction mixture is to be permitted to stand long enough for alkyl ester to separate into an upper phase overlying a lower phase mixture comprised of particulates and product glycerol. The temporary holding tank 85 is a closed vessel with a conical bottom 85B that terminates in a glycerol outlet port and a floating pickup 85P comprised of a flexible, open-ended hose attached to a hollow, polyethylene ball. The floating pickup 85P communicates through pipe 86 with the inlet side of the first intake manifold 18. Separation of the phases is aided by first cooling the reaction mixture. Therefore, the main pump 22 is activated, thereby causing reaction mixture to continuously circulate out of the reaction tank 50 through the main pump 22, thence through a chiller 91 connected to the outlet port 22o of the main pump 22 and from there back into the conical bottom 85B of the temporary holding tank 85 through tube 85T. The chiller 91 comprises a length of copper tubing surrounded by a water jacket or air cooling fins (not shown); the reaction mixture is conducted through the copper tubing and cold water is circulated through the water jacket. Once the reaction mixture has been adequately cooled and moved to the temporary holding tank 85, the main pump 22 is deactivated and the reaction mixture is permitted to stand long enough in the temporary holding tank 85 for alkyl ester to separate into an upper layer. The lower layer of product glycerol is drained from the temporary holding tank 85 through glycerol outlet port 87, thence through a transparent site tube 38 and through pipe 89 to the inlet side of a third intake manifold 400. The drainage through the port 87 is discontinued when it becomes apparent in the site tube 38 that alkyl ester is beginning to drain through port 87. The product glycerol is pumped from the third intake manifold 400 by a glycerol handling pump 93 through a third exhaust manifold 402 either directly to a glycerol storage tank 11 or, preferably, through pipe 404 and inlet port 406 to an upper portion of a closed, alcohol/glycerol separation tank 408. The tank 408 has a conical bottom 408B that terminates in a glycerol outlet port 410 through which glycerol drains back through pipe 412 to the inlet side of the third intake manifold 400. Glycerol in tank 408 is heated to 60-65 degrees C. and subjected to vacuum via a vacuum pump 175 through pipe 474 and return tee 475; see FIG. 7. Through this latter path, the glycerol can be pumped by the pump 93 through the tank 408 to promote escape of alcohol vapor from the glycerol. The alcohol vapor in the tank 408 is recaptured through an alcohol recovery system 161, as described below. For safety, the tank 408 is also fitted with an explosion damper and flame retarder 55.

Figure 2:
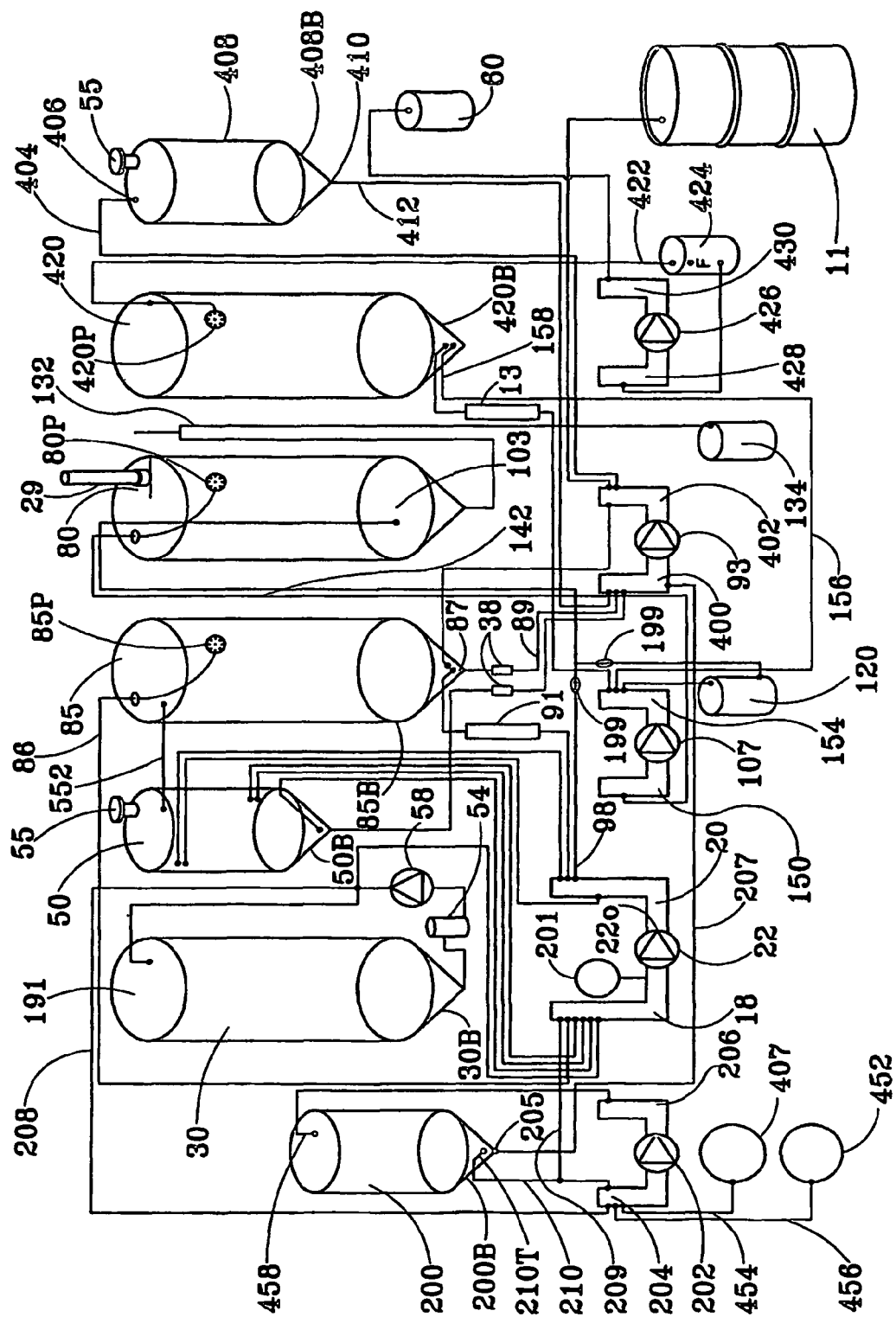
FIG. 2 is a schematic depiction of a second, more complete apparatus for esterifying free fatty acids in vegetable and/or animal oil to product alkyl ester as well as for transesterifying triglycerides in the oil to alkyl ester.

By activating the main pump 22, the upper layer of alkyl ester in the temporary holding tank 85 is drawn off through the floating pickup 85P, through the first intake manifold 18, the main pump 22, and the first exhaust manifold 20, and thence is conducted by pipe 98 to an inlet port 103 of a wash tank 80; see FIG. 2. The wash tank 80 is a closed vessel, preferably of clear plastic such as polyethylene, having a conical bottom 80B that terminates in a drain port 104. In an upper, interior portion of the wash tank 80 is a mister nozzle 125 through which water is sprayed down upon product alkyl ester 126 in the form of a mist 127 to wash out impurities. Adjacent the drain port 104 is an air inlet port 130 through which air bubbles are conducted from the vacuum pump 175. The air bubbles emerge inside the wash tank conical bottom 80B as a bubble cloud through a loop of hose with multiple perforations 130L. The wash tank 80 is equipped with a floating pickup 80P that communicates through a first, upper outlet port 105 with the inlet port 106 of a wash cycle pump 107 for recirculating an upper phase of washed alkyl ester via pump outlet port 108 through a heat exchanger 13, and through an activated charcoal canister 120 with a return path back into the wash tank 80. Attached to the drain port 131 is an antisiphon tube 132 for draining the lower, water layer from the wash tank 80 to a waste water receptacle and grease trap 134. Once the desired number of batches of product alkyl ester are accumulated within the interior of the wash tank 80, the wash cycle is carried out as follows. The spray mist is turned on, and a stream of air bubbles is introduced into the wash tank conical bottom 80B for about two hours. The water is permitted to settle to the bottom of the tank 80 and then drained. The same misting, bubbling, settling and draining steps are then repeated twice more to yield a washed, product alkyl ester.

The washed, product alkyl ester is conducted through the floating pickup 80P via pipe 142 to the inlet side of a second intake manifold 150; from there it is pumped by the wash cycle pump 107 through a second exhaust manifold 154 via pipe 156 to an inlet port 158 in a conical bottom 420B of a closed, settling tank 420. The washed, product alkyl ester is permitted to stand in the settling tank 420 long enough for said product to separate into an upper phase of alkyl ester overlying a lower phase comprised of unreacted triglycerides and particulates. The upper phase is drawn through the floating pickup 420P via pipe 422 through a filter 424 by activation of a filter pump 426 interposed between a fourth intake manifold 428 and a fourth exhaust manifold 430 and thence pumped to a day tank 60.

Figure 7:
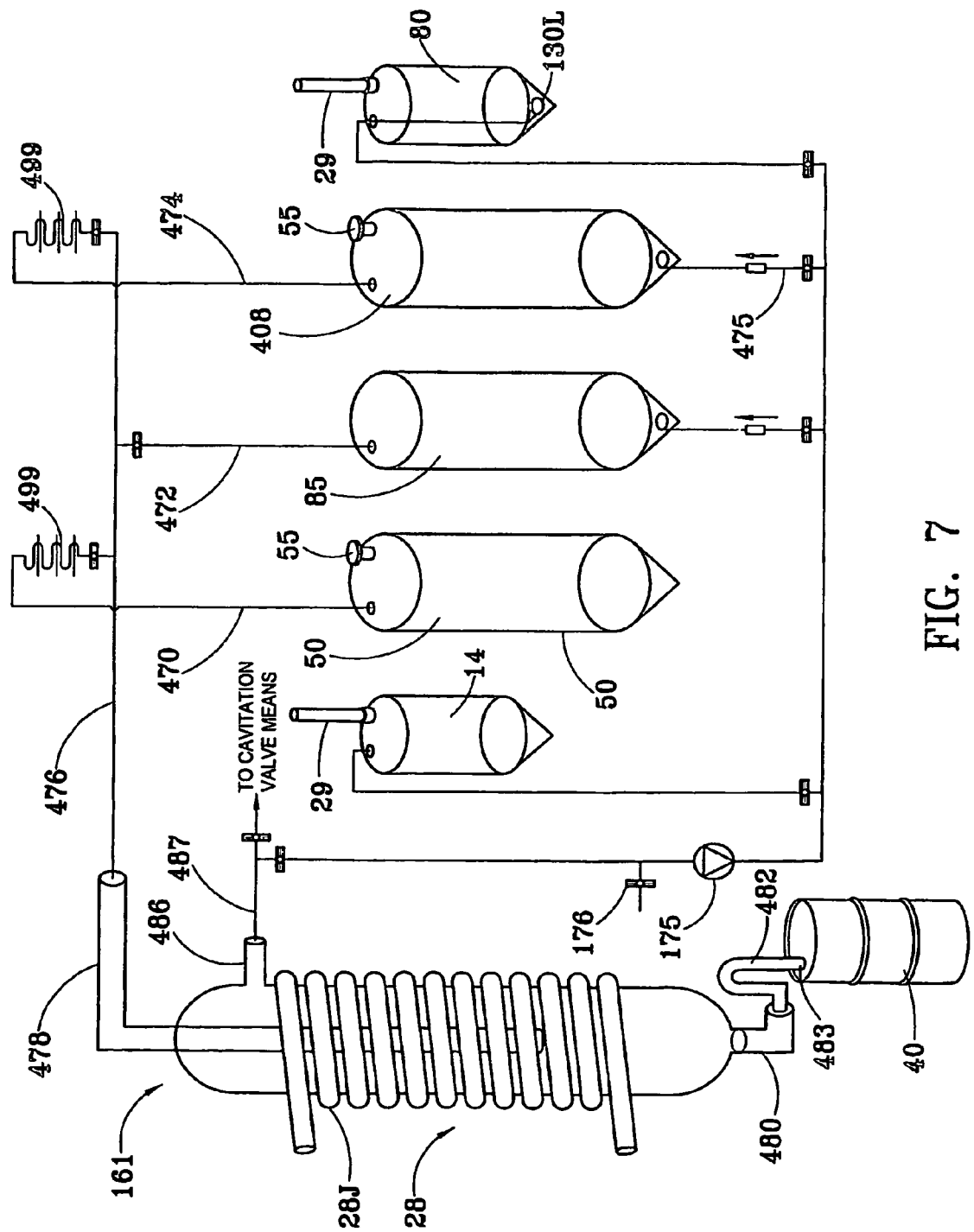
FIG. 7 is a schematic view of the alcohol recovery system and the wash bubbler loop.
Figure 8:
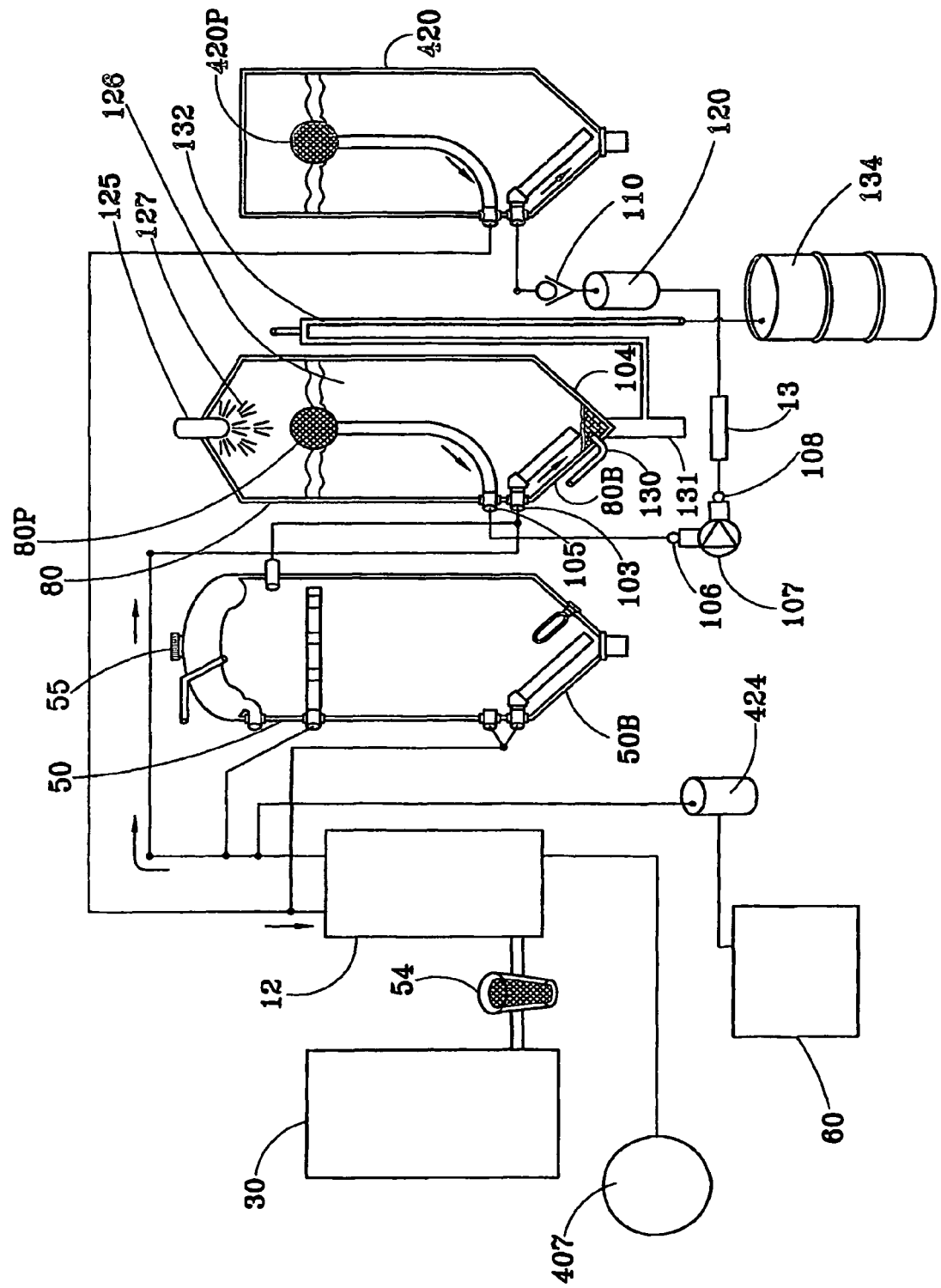
FIG. 8 is a schematic view of the reaction vessel, wash tank and settling tank, showing the floating pickups.

An alcohol recovery system 161 is provided as illustrated in FIG. 7. Alcohol vapor is conducted from upper portions of each of the reaction vessel 50, temporary holding tank 85 and alcohol/glycerol separation tank 408 via pipes 470, 472, 474, 476 to an inlet port 478 of alcohol condenser 28. The condenser 28 is surrounded by a water cooling coil 28J or air cooling fins and has a lower outlet port 480 to permit reclaimed liquid alcohol to exit the condenser. Reclaimed liquid alcohol drains through a drain trap air lock 482 into a reclaimed alcohol reservoir 40. The air lock 482 blocks air passage into the condenser 28 to maintain vacuum on the reaction vessel 50 and to keep the alcohol recovery system 161 closed. The condenser 28 also has an upper outlet port 486 that communicates with the interior, conical bottoms of the temporary holding tank 85 and alcohol/glycerol separation tank 408. These connections to tanks 85 and 408 are made in order to replenish the air to those tanks as it is being withdrawn by the mechanical vacuum pump 175, which is also in communication with the condenser upper outlet port 486 via pipe 487. The condenser upper outlet port 486 also communicates with an upper, interior portion of the base catalyst tank 14 through the vacuum pump 175 in order to chase vapors from said tank through the vent tube 29. In this manner, the vacuum pump 175 serves to create a vacuum to suck air and alcohol vapor from upper portions of each of the tanks 50, 85, 408 and to return the same air to the same tanks, which preserves the desired closed status of the apparatus of the invention. An air bleed valve 176 is provided to supply air from the atmosphere to the vacuum pump 175 when the vacuum pump 175 is bubbling air into the wash tank 80.

To guard against explosion or flame reaching the condenser 28, the alcohol recovery system 161 further comprises a baffle 499 interposed between the condenser 28 and the alcohol/glycerol separation tank 408 and another baffle 499 between the condenser 28 and the transesterification reaction vessel 55; FIG. 7. Each of the baffles 499 includes tortuous tubing and cooling fins to retard flames and to promote cooling of alcohol vapor. The baffles 499 are oriented vertically to promote drainage of liquified alcohol toward the condenser inlet port 478.

The foregoing description applies to a method and apparatus for transesterification of animal and/or vegetable oil that consists essentially of triglycerides with little or no free fatty acids or water. To produce biodiesel fuel from animal and/or vegetable oil that contains, in addition to triglycerides, free fatty acids and water, such as will ordinarily be the case with cooked edible oil, it is necessary to remove the water and to esterify the free fatty acids prior to initiating the transesterification reaction. Referring now to FIG. 2, a closed esterification flow system 171 is depicted comprising an esterification reaction vessel 200 having a conical bottom 200b that terminates in a glycerol drain port 205, an esterification flow pump 202 interposed between and in communication with a fifth intake manifold 204 and a fifth exhaust manifold 206. Heated oil is pumped from tank 30 by pump 58 via pipe 208 to the inlet side of the fifth intake manifold 204 and thence flows via pipe 210 into the esterification reaction vessel 200. With reference to FIG. 9, the pump 405 is activated and valves 409 and 43 are opened to pump alcohol from the alcohol primer 40 and the alcohol reservoir 407 through pipe 419 to the esterification flow system 171. The esterification flow pump 202 is activated to mix alcohol and oil thoroughly. Esterification catalyst, such as concentrated sulfuric acid, is drawn into the esterification flow system 171 from an acid reservoir tank 452 via pipes 454 and 456, respectively, into the inlet side of the fifth intake manifold 204. These reagents then flow through the pump 202, out the fifth exhaust manifold 206 to an inlet port 458 in an upper portion of the esterification reaction vessel 200. A draw tube 210T in communication with pipe 210 extends into the conical bottom 200B of the esterification reaction vessel 200. As the esterification pump 202 continues to run, esterification reaction mixture, comprising triglycerides, catalyst, alkyl alcohol, free fatty acids, and product alkyl ester, continuously recirculates into and out of the vessel 200. After the esterification reaction is complete, the pump 202 is deactivated, and the contents of the esterification flow system are permitted to stand. Glycerol that forms a lower layer in the vessel 200 is drained out the drainage port 205 and is conducted via pipe 207 to the inlet side of the third intake manifold 400. The upper layer in the vessel 200 is then conducted to the inlet side of the first intake manifold 18 by pipe 209 ready for use in a transesterification reaction in vessel 50 and for subsequent processing as described above. An alcohol drum-mounted pump 423 can alternatively supply alcohol to the transesterification flow system 201 via pipe 499 as shown in dashed outline in FIG. 9.

Figure 4:
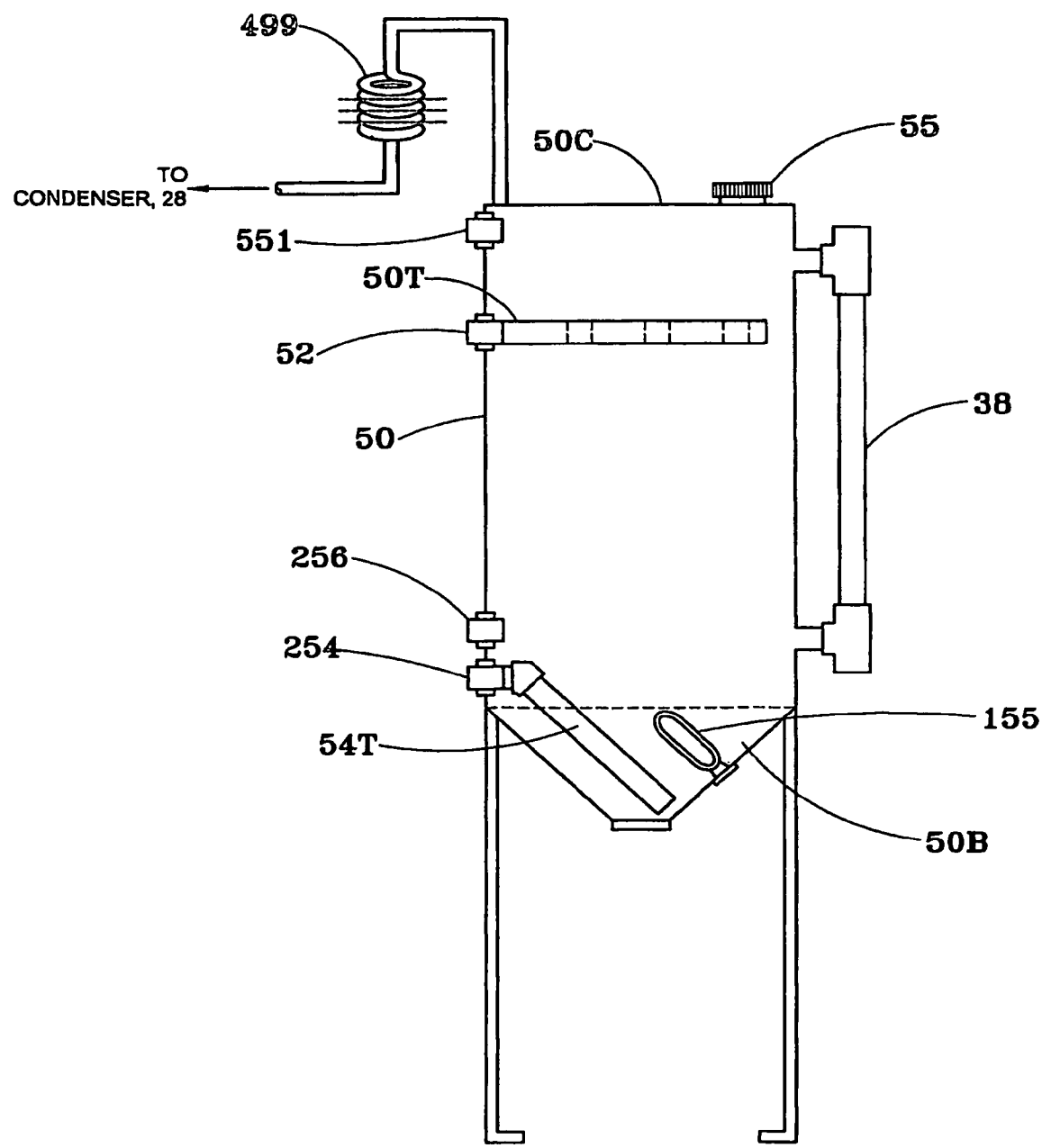
FIG. 4 is a cross-sectional view of the transesterification reaction vessel.
Figure 11:
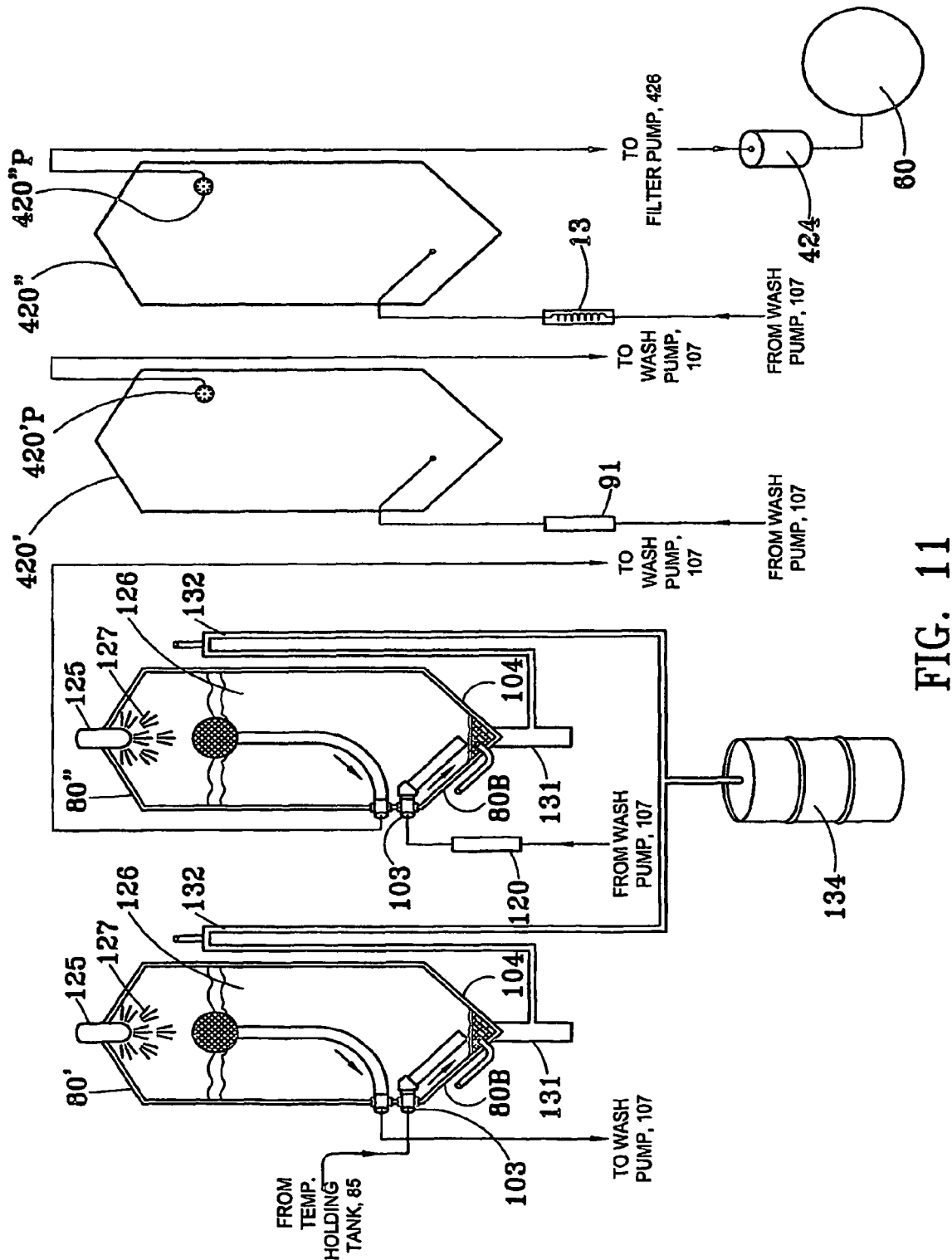
FIG. 11 is a partial schematic depiction of alternate apparatus for purifying product alkyl ester in dual washing and settling tanks.

Having hereby disclosed the subject matter of the present invention, it should be apparent that many modifications, substitutions, and variations of the present invention are possible in light thereof. The main pump 22 preferably is of centrifugal type with low pressure and high volume throughput because a gear type pump is more likely to be corroded by cavitation. All pumps should be sealed to lessen fire and explosion hazards. It is found that alkyl ester that is washed in a single wash tank 80 as described above tends to precipitate out soaps if allowed to stand in a cold environment. Accordingly, production of biodiesel fuel from animal and/or vegetable oil for winter use in cold climates can be improved by washing the alkyl ester serially in two separate tanks 80' and 80" instead of in a single wash tank 80, followed by settling serially in two separate settling tanks 420', 420" as depicted in FIG. 11. In the first wash tank 80', after misting and air bubbling, the product alkyl ester is permitted to stand for a period of time adequate to permit settling out of soaps and water. The product alkyl ester is then decanted and conducted through an activated charcoal canister 120 and thence to a second wash tank 80", subjected again to misting and air bubbling as before, and allowed to settle once again as before. The product alkyl ester is then decanted and conducted to a first settling tank 420' whose base is chilled to 10 degrees C., more or less, and permitted to settle. The product alkyl ester is decanted, conducted through a heat exchanger 13 to warm it, and on to a second settling tank 420" where it is permitted to settle once again. The alkyl ester is then decanted from the second settling tank 420", filtered and stored in a day tank 60. Moreover, in addition to the batch mode of operation described above, the method and apparatus can be adapted to continuous mode. As shown in FIG. 4, a reaction vessel outlet port 551 is provided through which reaction mixture can be conducted to the settling tank 85 via pipe 552, as shown in FIG. 2. Photoelectric sensing means can be installed adjacent the reaction vessel conical bottom 50B to sense the clarity of glycerol accumulating therein and to activate a valve (not shown) to open and permit glycerol to drain; thereafter, said sensing means will sense, by the shift to higher clarity when the glycerol is substantially all drained away and alkyl ester begins to drain from the reaction vessel 50, an increase in light transmitted through said conical bottom 50B, and activate said valve to close. The invention can be further modified by also including cavitation valve means in the esterification flow system 171. That may be done by including another adjustable air bleed valve 112 and another check valve 110 in series with the inlet side of the fifth intake manifold 204 in order to provide a stream of air bubbles with accompanying slight cavitation to the esterification flow system 171. The esterification reaction vessel 200 could also be provided with a vent tube 29 to vent sulfuric acid vapor to the atmosphere. Alternatively, the esterification reaction vessel 200 and the fifth manifold assembly 202, 204, 206 could be eliminated and the esterification reaction could proceed in the transesterification reaction vessel 50 instead. This might be done by providing additional inlet ports on the first intake manifold 18—one to introduce esterification catalyst and one to introduce alkyl alcohol—and by utilizing the main pump 22 to recirculate the esterification reaction mixture through the reaction vessel 50.

Thus, it is to be understood that the present invention can be practiced other than as specifically described and should be limited in scope and breadth only by the appended claims. It will be further understood that, in the claims, oil described as "consisting essentially of triglycerides" is defined to mean that the primary constituents of the oil are triglycerides but that other constituents may be present as well; similarly, oil described as "consisting essentially of triglycerides, free fatty acids and water" is defined to mean that the primary constituents of the oil are triglycerides, that said oil has other constituents, and among those other constituents are free fatty acids and water.

I claim:

1. A biodiesel refining apparatus for creating alkyl ester from oil comprising fatty acid triglycerides, comprising:
    a preheater tank suitable for storing and preheating oil, said tank including a heat exchanger;
    means for preheating an oil;
    a base catalyst tank for creating a transesterification catalyst, said tank having a narrowed bottom, an inlet port for receiving alcohol, an outlet port, a funnel opening for receiving base, and a plurality of spaced-apart jets in communication with said inlet port and angled tangentially and downward suitable to induce swirling of alcohol and base in said narrowed bottom; and
    a closed, recirculating transesterification flow system, said flow system including
        a reaction vessel having at least one inlet port in an upper portion thereof and at least one outlet port in a lower portion thereof, recirculating means to conduct a reactant mixture from the reaction vessel out said outlet port through an external recirculation loop and back in to the reaction vessel through said inlet port, and a glycerol drain for draining away glycerol formed during transesterification;
        valve means suitable for controlling entry of preheated oil, alcohol and transesterification catalyst into said transesterification flow system; and
        cavitation valve means for introducing slight cavitation into the transesterification flow system to promote a rapid and complete transesterification.

2. The apparatus of claim 1, wherein the reaction vessel has a first outlet port through which the recirculating means conducts the reaction mixture and a second outlet port through which a draw tube extends down into the narrowed bottom of the reaction vessel, whereby said recirculation means also conducts the reaction mixture from said conical bottom through said draw tube.

3. The apparatus of claim 2, further comprising an alcohol/alkoxide circulation means external to, and in communication with, the base catalyst tank, through which an alkyl alcohol and alkoxide mixture can continuously circulate.

4. The apparatus of claim 3, further comprising a temporary holding tank for receiving and temporarily storing reaction mixture from the reaction vessel to permit said mixture sufficient time to separate alkyl ester from glycerol prior to washing the alkyl ester.

5. The apparatus of claim 4 further comprising means to recover alcohol vapor from the reaction vessel, temporary holding tank, and alcohol/glycerol separation tank, including an alcohol condenser having an inlet port, an outlet port and an alcohol drain port, a drain trap air lock connected to said drain port, a vacuum pump having an inlet port in communication with the condenser outlet port and an outlet port in communication with lower, interior portions of the reaction vessel, holding tank and settling tank.

6. The apparatus of claim 1, wherein the cavitation valve means includes a one-way check valve and an adjustable air valve connected in series with, and intermediate, said condenser outlet port and the inlet port of the main pump.

7. The apparatus of claim 6, further comprising a cavitation air bleed valve intermediate the cavitation valve and the condenser outlet port.

8. The apparatus of claim 1, further comprising a chiller connected in series with the outlet port of the reaction vessel and the inlet port of a temporary holding tank for cooling the reaction mixture formed in the reaction vessel prior to separation of glycerol from alkyl ester in said temporary holding tank.

9. A biodiesel refining apparatus for creating alkyl ester from oil comprising fatty acid triglycerides, free fatty acids, and water, comprising:
    a preheater tank suitable for storing and preheating the oil, said tank including a heat exchanger;
    means for preheating an oil;
    a base catalyst tank for creating a transesterification catalyst, said tank having a narrowed bottom bottom, an inlet port for receiving alcohol, an outlet port, an opening for receiving base, and a plurality of spaced-apart jets in communication with said inlet port and angled tangentially and downward suitable to induce swirling of alcohol and base in said narrowed bottom;

a closed, recirculating transesterification flow system, said flow system including
a reaction vessel having at least one inlet port in an upper portion thereof and at least one outlet port in a lower portion thereof, recirculating means to conduct a reactant mixture from the reaction vessel out said outlet port through an external recirculation loop and back in to the reaction vessel through said inlet port, and a glycerol drain for draining away glycerol formed during transesterification;
valve means suitable for controlling entry of preheated oil and transesterification catalyst into said transesterification flow system; and
cavitation valve means for introducing slight cavitation into the transesterification flow system to promote a rapid and complete transesterification and
an esterification reaction system, including
an esterification reaction vessel having an oil inlet port in communication with said preheater tank, a reaction products outlet port, and a glycerol drain port;
esterification catalyst supply means in communication with said oil inlet port; and
valve means for conducting alkyl ester from said vessel to said transesterification flow system;

10. The apparatus of claim 9, further comprising a settling tank to receive and store washed alkyl ester long enough to permit settling out of soap particles, said tank being equipped with a drain for draining the soap particles and a floating pickup for drawing off the washed alkyl ester.

11. The apparatus of claim 10, further comprising an alcohol/alkoxide circulation means external to, and in communication with, the base catalyst tank, through which an alkyl alcohol and alkoxide mixture can continuously circulate.

12. The apparatus of claim 11, further comprising a temporary holding tank for receiving and temporarily storing reaction mixture from the reaction vessel prior to washing the alkyl ester.

13. The apparatus of claim 12, further comprising means to recover alcohol vapor from the reaction vessel, temporary holding tank, and alcohol/glycerol separation tank, said means including an alcohol condenser having an inlet port.

14. The apparatus of claim 9, wherein the cavitation valve means includes a one-way check valve and an air inlet valve connected in series with, and intermediate, said condenser outlet port and the inlet port of the main pump.

15. The apparatus of claim 14, further comprising a chiller connected in series with the outlet port of the reaction vessel and the inlet port of the temporary holding tank for cooling the reaction mixture formed in the reaction vessel prior to separation of glycerol from alkyl ester in said temporary holding tank.

16. The biodiesel refining apparatus of claim 1, further comprising:
a temporary holding tank suitable for permitting separation of reaction mixture into an upper phase of product alkyl ester overlying a lower phase comprised of unreacted triglycerides, glycerol and particulates, said tank having a glycerol drain for draining glycerol from the tank and a floating pickup for drawing off the product alkyl ester;
a wash tank suitable for washing the product alkyl ester, an upper portion of said tank having water mist spray means and a floating pickup and a lower portion of said tank having an air bubble entry port for receiving a stream of air bubbles and a drain for draining soaps, water and particulates; and
means for filtering particulates from the washed alkyl ester.

17. The biodiesel refining apparatus of claim 9, further comprising:
an alkyl ester/glycerol separation tank for permitting separation of reaction mixture into an upper phase of product alkyl ester overlying a lower phase mixture comprised of particulates and glycerol, said tank having a glycerol drain for draining glycerol from the tank;
a wash tank for washing the product alkyl ester, an upper portion of said tank having water mist spray means and a floating pickup for drawing off washed alkyl ester and a lower portion of said tank having an air bubble entry port for receiving a stream of air bubbles and a drain for draining soaps, water and particulates; and
means for filtering particulates from the washed alkyl ester.

18. A transesterification flow system comprising:
a reaction vessel;
a recirculator being fluidly coupled to the reaction vessel to remove fluid from the vessel and return the removed fluid to the vessel to provide a closed, recirculating transesterification flow system; and
an air inlet configured to introduce air into the recirculating transesterification fluid through cavitations valve means.

19. The system of claim 18, wherein the cavitation valve means is suitably configured to enable introduction of air in a manner to form bubbles into the recirculating transesterification fluid.

20. The system of claim 18, wherein the recirculator comprises a pump having an inlet port for receiving a reaction mixture from the reaction vessel and an outlet port for pumping a reaction mixture back to the reaction vessel, the cavitation valve means connected in series with the inlet port of the pump.

21. The system of claim 20, wherein the cavitation valve means includes a check valve and an adjustable, air inlet valve connected in series with the inlet port of the pump.

22. The system of claim 21, further comprising a condenser having a condenser inlet and a condenser outlet, the condenser inlet fluidly coupled to an upper part of the reaction vessel, the condenser outlet fluidly coupled to the air inlet valve of the cavitation valve means.

23. The system of claim 22, wherein the condenser is an alcohol condenser.

24. The system of claim 18 wherein the reaction vessel has a drain.

25. The system of claim 18, wherein the reaction vessel has a vent.

26. The system of claim 18 further comprising a transesterification catalyst tank having:
a base catalyst inlet configured to receive a base catalyst;
an alcohol inlet configured to receive an alcohol;
jets in communication with the alcohol inlet configured to introduce alcohol into contact with base in the catalyst tank; and
an outlet configured to allow passage of a transesterification catalyst from the catalyst tank.

27. The system of claim 26 wherein the transertification flow system further comprises:
a transesterification catalyst inlet coupled to the outlet of the catalyst tank; and
an oil inlet to receive oil.

* * * * *